United States Patent [19]

Berges

[11] 4,068,073

[45] Jan. 10, 1978

[54] 7-AMINO INTERMEDIATES FOR PREPARING 7-ACYL-3-(UREIDOALKYL SUBSTITUTED TETRAZOLYLTHIOMETHYL)-CEPHALOSPORINS

[75] Inventor: David A. Berges, Wayne, Pa.

[73] Assignee: SmithKline Corporation, Philadelphia, Pa.

[21] Appl. No.: 753,259

[22] Filed: Dec. 22, 1976

Related U.S. Application Data

[62] Division of Ser. No. 639,033, Dec. 9, 1975, Pat. No. 4,025,626.

[51] Int. Cl.$^2$ .................. A61K 31/545; C07D 501/18; C07D 501/36
[52] U.S. Cl. ...................................... 544/26; 424/246; 544/27
[58] Field of Search ...................... 260/243 C; 424/246

[56] References Cited

U.S. PATENT DOCUMENTS 3,819,623  12/1974  Takano et al. ................... 260/243 C
3,867,380   2/1975  Dunn et al. ...................... 260/243 C

FOREIGN PATENT DOCUMENTS 823,861   6/1975  Belgium.
2,415,402  10/1974  Germany.

Primary Examiner—Nicholas S. Rizzo
Attorney, Agent, or Firm—Janice E. Williams; William H. Edgerton; Alan D. Lourie

[57] ABSTRACT

The compounds of this invention are cephalosporins having various acyl substituents at the 7-position and an ureidoalkyl substituted tetrazolylthiomethyl group at the 3-position of the cephem nucleus and intermediates for the preparation thereof. The 7-acylated compounds have antibacterial activity.

4 Claims, No Drawings

7-AMINO INTERMEDIATES FOR PREPARING 7-ACYL-3-(UREIDOALKYL SUBSTITUTED TETRAZOLYLTHIOMETHYL)-CEPHALOSPORINS

This is a division of application Ser. No. 639,033, filed Dec. 9, 1975, now U.S. Pat. No. 4,025,626.

This invention relates to a new series of cephalosporin compounds which have antibacterial activity when administered parenterally and orally and to intermediates for the preparation thereof. In particular, the structures of the biologically active cephalosporin compounds of this invention are characterized by having an ureidoalkyl substituted tetrazolylthiomethyl group at the 3-position of the cephem nucleus. Also, this invention extends to methods and compositions for treating certain bacterial infections using these new compounds as well as to certain chemical intermediates and methods for preparing the compounds described hereafter.

The compounds of this invention are represented by the following structural formula:

FORMULA 1

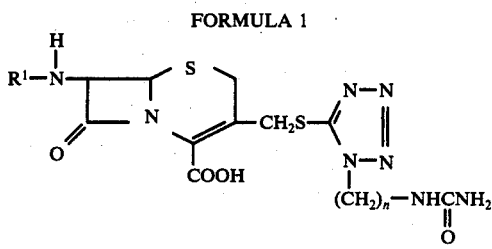

in which:

R$^1$ is an acyl group selected from the group consisting of:

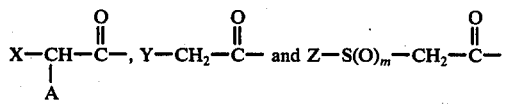

where:

X is thienyl, dihydrophenyl, phenyl or phenyl monosubstituted with hydroxy, hydroxymethyl, formamido, ureido or carboxymethylamino;

A is NH$_2$, OH, COOH or SO$_3$H; or formyloxy when X is phenyl;

Y is cyano, aminomethylphenyl, sydnone, pyridone, thienyl or tetrazolyl;

Z is methyl, trifluoromethyl, trifluoroethyl, pyridyl or cyanomethyl;

m is zero to two; and n is two to five, or a non-toxic pharmaceutically acceptable salt thereof.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such esters are included within the scope of this invention.

Preferred compounds of this invention are represented by Formula I where n is two.

Advantageous compounds of this invention are represented by Formula I where n is two and R$^1$ is

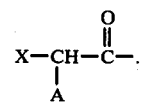

Most advantageous are the compounds represented by Formula I where n is two, R$^1$ is

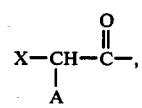

X is phenyl or hydroxyphenyl and A is NH$_2$ or OH.

Examples of the most preferred 7-acyl substituents (R$^1$NH—) of the compounds of Formula I are listed below:

α-hydroxyphenylacetamido
α-aminophenylacetamido
α-amino-4-hydroxyphenylacetamido
trifluoromethylthioacetamido
methylthioacetamido
2,2,2-trifluoroethylsulfinylacetamido
cyanoacetamido
α-carboxythienylacetamido
α-carboxyphenylacetamido
α-sulfophenylacetamido
methylsulfonylacetamido
cyanomethylthioacetamido
α-amino-4-carboxymethylaminophenylacetamido
2-aminomethylphenylacetamido
3-sydnoneacetamido
1-tetrazolylacetamido
2-thienylacetamido
2-pyridoneacetamido
4-pyridoneacetamido
4-pyridylthioacetamido.

Particularly preferred is the compound 7-D-mandelamido-3-[1-(2-ureidoethyl)tetrazol-5-ylthiomethyl]-3-cephem-4-carboxylic acid.

Cephalosporin derivatives having 7-acyl substituents as defined above are well documented in the prior art. Substitution by variously substituted S-heterocyclicthiomethyl groups (—CH$_2$SHet) at the 3-position of the cephem nucleus is also known. Belgian Pat. No. 823,861 generically disclosed 7-[2-(2-exo-substituted-4-thiazolin-4-yl)acetamido]cephalosporins having, among others, a tetrazolylthiomethyl group at the 3-position which may be substituted by, inter alia, a N-carbamoyl substituted aminoalkyl group. No examples or other specific disclosure of any compound containing such a N-carbamoyl substituted aminoalkyl substituent on any 3-heterocyclic thiomethyl group are present in the reference. No other references to cephalosporin compounds containing the 3-(ureidoalkyl substituted tetrazolyl)thiomethyl moiety disclosed herein are believed to be known to the art.

The compounds of Formula I are prepared by acylation of an appropriate 7-amino-3-ureidoalkyltetrazolylthiomethyl cephalosporin nucleus of Formula II:

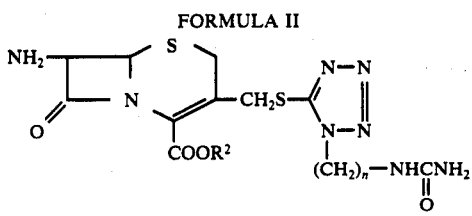

FORMULA II in which:

n is two to five; and

R[2] is hydrogen or a protecting ester group,
with an appropriate acylating agent followed by removal of the protective groups when present. The carboxylic acid group of the acylating agent is activated by any of the standard methods such as conversion to the mixed anhydride, acid chloride, acid imidazolide or activated ester. In addition, a reagent such as dicyclohexylcarbodiimide can be used provided that the carboxyl group on the cephem nucleus is protected with an easily removable protecting group such as a benzhydryl, t-butyl, trichloroethyl, benzyl, benzyloxymethyl, p-methoxybenzyl or p-nitrobenzyl ester. When A is NH$_2$, the α-amino group of the acylating agent is, preferably, protected prior to acylation with an easily removable protective group known in the art such as t-butoxycarbonyl, trichloroethoxycarbonyl, benzyloxycarbonyl, the methyl acetoacetate adduct or similar groups commonly used in the synthesis of peptides. The compounds represented by Formula II above are also considered as objects of this invention.

Alternatively, the compounds of Formula I are prepared by acylating 7-aminocephalosporanic acid with an appropriately protected acylating agent, as described above, and then displacing the 3-acetoxy group with the desired ureidoalkyltetrazole thiol with subsequent removal of the protective group(s). The ureidoalkyltetrazole thiols of the formula:

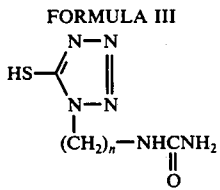

FORMULA III in which n is two to five,
are also objects of this invention, being important intermediates for producing pharmaceutical end products as described herein.

The protective groups can be removed according to methods well known to the art, such as with trifluoroacetic acid when t-butyl or t-butoxycarbonyl protective groups are used. The resulting salt is converted to the zwitterionic product or to the free acid by means of a basic ion exchange resin such as polystyrene-amine ion exchange resin (Amberlite IR-45) or else by basification of an aqueous solution of the salt.

The acylating agents used as starting materials are either known or prepared by known methods.

The 7-amino-3-ureidoalkyltetrazolylthiomethyl cephalosporin starting materials of Formula II are prepared by reaction of 7-aminocephalosporanic acid and an ureidoalkyltetrazole thiol of Formula III and then esterified.

The ureidoalkyltetrazole thiols of Formula III are prepared by reaction of the corresponding 1-aminoalkyl-5-(2,4-dinitrophenylthio)tetrazole compounds, prepared from 2,4-dinitrofluorobenzene and an 1-acetamidoalkyltetrazole-5-thiol followed by acid hydrolysis of the acetamido moiety with cyanic acid, which is prepared for example from potassium cyanate and acetic acid, with subsequent cleavage of the 2,4-dinitrophenyl protecting group. The 1-acetamido-alkyltetrazole-5-thiols are prepared by reaction of an acetamidoalkyldithiocarbamate such as methyl 2-acetamidoethyldithiocarbamate with an azide such as sodium azide The acetamidoalkyldithiocarbamates are prepared by treatment of an N-aminoalkylacetamide such as N-(2-aminoethyl)acetamide with carbon disulfide and an alkyl halide such as methyl iodide in the presence of a base such as triethylamine.

Certain compounds of this invention are capable of forming salts with, for example, the alkali metals such as sodium or potassium, the alkaline earth metals such as calcium or with the ammonium cation. When A is NH$_2$, the compounds can exist as the zwitterion or as either an acid or base salt. These salts are prepared by standard methods using a wide variety of non-toxic pharmaceutically acceptable acids and bases known in the art and are also considered as objects of this invention.

It will be recognized that due to the asymmetric α-carbon atom in the 7-acetamido group of Formula I when R[1] is

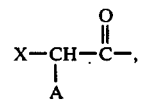

optical isomers will exist. Racemic or resolved products are obtained depending upon whether a racemic or resolved sidechain acid is used as an acylating agent. The resolved sidechain acids are readily obtained from the racemic compounds by resolution according to well known methods, including fractional crystallization of a salt formed with an optically active acid or base. All of the isomers, including separated isomers and mixtures thereof, are included within the scope of this invention.

The compounds of Formula I have exceptional antibacterial activity against both Gram-positive and Gram-negative organisms. Minimum inhibitory concentrations (MIC's) range from 0.1 to >200 μg./ml. in in vitro testing. Test results for the compound 7-D-mandelamido-3-[1-(2-ureidoethyl)tetrazol-5-ylthiomethyl]-3-cephem-4-carboxylic acid are given below:

| Bacteria | MIC (μg./ml.) |
| --- | --- |
| S. aureus HH 127 | 3.1, 1.6 |
| S. aureus SK 23390 | 0.4, 0.4 |
| S. villaluz SK 70390 | 25, 25 |
| Strep. faecalis HH 34358 | 25, 25 |
| E. coli SK 12140 | 0.8, 0.8 |
| E. coli HH 33779 | 1.6, 1.6 |
| Kleb. pneumo. SK 4200 | 0.8, 0.8 |
| Kleb. pneumo. SK 1200 | 0.4, 0.4 |
| Salmonella ATCC 12176 | 0.8, 0.2 |
| Shigella HH 117 | 0.1, 0.2 |
| Pseudo. aerug. HH 63 | >200, >200 |
| Serratia Marc. ATCC 13880 | 25, 25 |
| Proteus morgani 179 | 0.8, 0.8 |
| Entero aerog. ATCC 13048 | 1.6, 6.3 |
| Entero. cloacae HH 31254 | 0.8, 0.8 |

In the in vivo mouse protection test, 7-D-mandelamido-3-[1-(2-ureidoethyl)tetrazol-5-ylthiomethyl]-

3-cephem-4-carboxylic acid exhibited $ED_{50}$'s of 0.86 mg./kg. against E. coli 12140 and 1.34 mg./kg. against Kleb. pneumo. 4200 upon subcutaneous injection; and 17.5 mg./kg. against E. coli 12140 and 25.5 mg./kg. against Kleb. pneumo. 4200 upon oral administration.

Pharmaceutical compositions having antibacterial activity which comprise a pharmaceutical carrier containing an active but non-toxic quantity of a compound of Formula I as well as methods of combatting bacterial infections by administering such a composition to an infected host in a non-toxic amount sufficient to combat such infections are also objects of this invention. The administration may be orally or by parenteral injection such as subcutaneously, intramuscularly or intravenously. The injection of suitably prepared sterile solutions or suspensions containing an effective, non-toxic amount of the new cephalosporin compound is the preferred route of administration.

The compounds of Formula I are formulated and administered in the same manner as other cephalosporins. The dosage regimen comprises administration, preferably by injection, or an active but non-toxic quantity of a compound of Formula I selected from the dosage unit range of from 100 to 1000 mg. with the total daily dosage regimen being from 400 mg. to 6 g. The precise dosages are dependent upon the age and weight of the subject and on the infection being treated and can be determined by those skilled in the art based on the data disclosed herein compared with that available to the art attained with known cephalosporins.

The following examples illustrate the invention but are not to be construed as limiting the scope thereof. Temperatures are in degrees Centigrade (° C.) unless otherwise stated.

EXAMPLE 1

7-D-Mandelamido-3-[1-(2-ureidoethyl)tetrazol-5-ylthiomethyl]-3-cephem-4-carboxylic acid To a solution of 20.4 g. (0.20 mol.) of N-(2-aminoethyl)acetamide in 200 ml. of 95% ethanol was added 27.9 ml. (0.20 mol.) of triethylamine and 12.0 ml. (0.20 mol.) of carbon disulfide. The exothermic reaction reached reflux and then was cooled to ambient temperature over a 1.5 hour period. Methyl iodide (28.4 g., 0.20 mol.) was added which again produced an exothermic reaction. After 1.75 hours the reaction mixture was evaporated to dryness and the solid residue was dissolved in 200 ml. of water. The aqueous solution was extracted twice with 250 ml. portions of ethyl acetate. The extracts were combined, shaken with sodium thiosulfate, dried (MgSO₄) and evaporated to dryness to give methyl 2-acetamidoethyldithiocarbamate.

To a solution of 38.4 g. (0.198 mol.) of methyl 2-acetamidoethyldithiocarbamate in 100 ml. of 95% ethanol was added a solution of 13.5 g. (0.208 mol.) of sodium azide in 100 ml. of water. The reaction mixture was refluxed for 24 hours then cooled and concentrated under reduced pressure to about half volume. The solution was cooled to 15°, 50 ml. of 6N sulfuric acid was added and the acidic solution was filtered. The filtrate was concentrated to about 100 ml., chilled at 5° and 1-(2-acetamidoethyl)tetrazol-5-thiol was collected, m.p. 139°-139.5°. Additional amounts of the product were obtained by continuous extraction of the filtrate with ethyl acetate.

A solution of 9.3 g. (0.050 mol.) of 2,4-dinitrofluorobenzene in 50 ml. of acetone was added to a solution of 9.35 g. (0.050 mol.) of 1-(2-acetamidoethyl)tetrazole-5-thiol and 6.85 ml. (0.050 mol.) of triethylamine in 100 ml. of acetone and the reaction mixture was stirred for 1 hour. The solid was collected and recrystallized from acetonitrile to give 1-(2-acetamidoethyl)-5-(2,4-dinitrophenylthio)tetrazole, m.p. 197°-198°.

A mixture of 6.5 g. (0.02 mol.) of 1-(2-acetamidoethyl)-5-(2,4-dinitrophenylthio)tetrazole, 100 ml. of 12 N hydrochloric acid and 100 ml. of 95% ethanol was refluxed for 4.5 hours. The mixture was evaporated to dryness to give a gummy residue which crystallized upon addition of ethanol to give 1-(2-aminoethyl)-5-(2,4-dinitrophenylthio)-tetrazole hydrochloride, m.p. 217°-219° (d).

To a solution of 0.84 g. (0.010 mol.) of sodium bicarbonate and 0.81 g. (0.010 mol.) of potassium cyanate in 35 ml. of water containing 2.5 ml. of glacial acetic acid was added 3.15 g. (0.010 mol.) of 1-(2-aminoethyl)-5-(2,4-dinitrophenylthio)tetrazole hydrochloride. The mixture was refluxed for 2.5 hours, then it was filtered and the solid product was washed with water and recrystallized from methanol-acetone to give 5-(2,4-dinitrophenylthio)-1-(2-ureidoethyl)tetrazole, m.p. 190°-191° (d).

A mixture of 10 g. (0.031 mol.) of 5-(2,4-dinitrophenylthio)-1-(2-ureidoethyl)tetrazole and 60 ml. (0.055 mol.) of 5% sodium methoxide in methanol was stirred for 2.5 hours. An additional 35 ml. (0.031 mol.) of sodium methoxide solution was added and the mixture was stirred at 25° for 12 hours. Ether (ca. 2 L.) was added to the reaction mixture and the crystallized product was collected, washed with ethyl acetate and recrystallized from methanol-ether to give 1-(2-ureidoethyl)tetrazole-5-thiol sodium salt, m.p. 131°-134°.

$C_4H_7N_6OS$ . Na . 1 $H_2O$ 
Calculated: 21.05% C; 3.98% H; 36.83% N,
Found: 20.97% C; 4.04% H; 36.76% N.

A solution of 1-(2-ureidoethyl) tetrazole-5-thiol sodium salt in water is passed through an Amberlite IR-120H ion exchange resin column to give, after lyophilization, 1-(2-ureidoethyl)tetrazole-5-thiol.

A mixture of 1.5 g. (0.071 mol.) of 1-(2-ureidoethyl)-tetrazole-5-thiol sodium salt and 2.14 g. (0.005 mol.) of 7-D-mandelamidocephalosporanic acid sodium salt in 25 ml. of water was heated at ca. 80° for 2.5 hours. The reaction mixture was passed through a XAD-8 resin column while eluting with water and then methanol. The product-containing aqueous fractions were lyophilized to give 7-D-mandelamido-3-[1-(2-ureidoethyl)tetrazol-5-ylthiomethyl]-3-cephem-4-carboxylic acid sodium salt hydrate.

$C_{20}H_{21}N_8O_6S_2$ . Na . 2.5 $H_2O$ 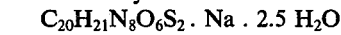
Calculated: 39.89% C; 4.32% H; 18.61% N;
Found: 39.98% C; 3.86% H; 18.51% N.

An aqueous solution of 7-D-mandelamido-3-[1-(2-ureidoethyl)tetrazol-5-ylthiomethyl]-3-cephem-4-carboxylic acid sodium salt is acidified with 3 N HCl to pH 2.5 and extracted with ethyl acetate. The extract is dried over anhydrous magnesium sulfate and evaporated to dryness to give the title compound.

EXAMPLE 2

7-(D-α-Aminophenylacetamido)-3-[1-(2-ureidoethyl)-tetrazol-5-ylthiomethyl]-3-cephem-4-carboxylic acid A solution of 7.58 g. (0.015 mol.) of 7-(D-α-t-butoxycarbonylaminophenylacetamido)cephalosporanic acid 1.88 g. (0.01 mol.) of 1-(2-ureidoethyl)tetrazole-5-thiol and 2.52 g. (0.03 mol.) of sodium bicarbonate in 125 ml.

of water is stirred at 60° for 5 hours while maintaining the pH at 7.0–7.2 by addition of sodium bicarbonate. The mixture is cooled and extracted with ethyl acetate. The aqueous phase is acidified to pH with 3N hydrochloric acid and the acidic solution is extracted again with ethyl acetate. The extract is dried (MgSO$_4$), filtered and evaporated to dryness to give 7-(D-α-t-butoxycarbonylaminophenylacetamido)-3-[1-(2-ureidoethyl)-tetrazol-5-ylthiomethyl]-3-cephem-4-carboxylic acid.

7-(D-α-t-Butoxycarbonylaminophenylacetamido)-3-[1-(2-ureidoethyl)tetrazol-5-ylthiomethyl]-3-cephem-4-carboxylic acid (ca. 1 g.) is stirred at 25° with 25 ml. of trifluoroacetic acid and 25 ml. of 1,3-dimethoxybenzene for 2.5 hours. The mixture is evaporated to dryness, ether is added to the residue and the precipitate is collected, washed with ether, stirred in acetonitrile for 2 hours, then collected and dried in vacuo to give the title compound as its trifluoroacetic acid salt. The salt is dissolved in water and the solution is stirred with IR-45 ion exchange resin then lyophilized to give the title compound.

EXAMPLE 3

Reaction of the N-t-butoxycarbonyl derivative of the following cephalosporanic acids:

7-(α-amino-4-hydroxyphenylacetamido)cephalosporanic acid
7-(α-amino-4-formamidophenylacetamido)cephalosporanic acid
7-(α-amino-3-formamidophenylacetamido)cephalosporanic acid
7-(α-amino-4-ureidophenylacetamido)cephalosporanic acid
7-(α-amino-4-ureidophenylacetamido)cephalosporanic acid
7-(α-amino-3-ureidophenylacatamido)cephalosporanic acid
7-(α-amino-4-hydroxymethylphenylacetamido)cephalosporanic acid
7-(α-amino-1,4-cyclohexadienylacetamido)cephalosporanic acid
7-(α-amino-4-carboxymethylaminophenylacetamido)-cephalosporanic acid with 1-(2-ureidoethyl)tetrazole-5-thiol as described in the procedure of Example 2 followed by removal of the protective group and conversion of the trifluoroacetic acid salt to the free acid as described therein gives the following compounds of this invention:

7-(α-amino-4-hydroxyphenylacetamido)-3-[1-(2-ureidoethyl)tetrazol-5-ylthiomethyl]-3-cephem-4-carboxylic acid
7-(α-amino-4-formamidophenylacetamido)-3-[1-(2-ureidoethyl)tetrazol-5-ylthiomethyl]-3-cephem-4-carboxylic acid
7-(α-amino-3-formamidophenylacetamido)-3-[1-(2-ureidoethyl)tetrazol-5-ylthiomethyl]-3-cephem-4-carboxylic acid
7-(α-amino-4-ureidophenylacetamido)-3-[1-2-ureidoethyl)tetrazol-5-ylthiomethyl]-3-cephem-4-carboxylic acid
7-(α-amino-3-ureidophenylacetamido-3-[1-(2-ureidoethyl)tetrazol 5-ylthiomethyl]-3-cephem-4-carboxylic acid
7-(α-amino-4-hydroxymethylphenylacetamido)-3-[1-(2-ureidoethyl)tetrazol-5-ylthiomethyl]-3-cephem-4-carboxylic acid
7-(α-amino-1,4-cyclohexadienylacetamido)-3-[1-(2-ureidoethyl)tetrazol-5-ylthiomethyl]-3-cephem-4-carboxylic acid
7-(α-amino-4-carboxymethylaminophenylacetamido)-3-[1-(2-ureidoethyl)tetrazol-5-ylthiomethyl]-3-cephem-4-carboxylic acid.

EXAMPLE 4

7-(4-Hydroxymandelamido)-3-[1-(2-ureidoethyl)tetrazol-5-ylthiomethyl]-3-cephem-4-carboxylic acid is prepared by reaction of 7-(4-hydroxymandelamido)-cephalosporanic acid sodium salt and 1-(2-ureidoethyl)-tetrazole-5-thiol sodium salt as described in the procedure of Example 1 followed by conversion of the product sodium salt to the free acid as described therein.

EXAMPLE 5

When the sodium salt of a cephalosporanic acid listed below:

7-(3-sydnoneacetamido)cephalosporanic acid
7-(2-thienylacetamido)cephalosporanic acid
7-(1-tetrazolylacetamido)cephalosporanic acid is reacted with 1-(2-ureidoethyl)tetrazole-5-thiol sodium salt by the procedure described in Example 1 and the product is converted to the free acid as described therein, the following compounds of this invention are obtained, respectively:

7-(3-sydnoneacetamido)-3-[1-(2-ureidoethyl)tetrazol-5-ylthiomethyl]-3-cephem-4-carboxylic acid
7-(2-thienylacetamido)-3-[1-(2-ureidoethyl)tetrazol-5-ylthiomethyl]-3-cephem-4-carboxylic acid
7-(1-tetrazolylacetamido)-3-[1-(2-ureidoethyl)tetrazol-5-ylthiomethyl]-3-cephem-4-carboxylic acid.

EXAMPLE 6

7-(2-Aminomethylphenylacetamido)-3-[1-(2-ureidoethyl)tetrazol-5-ylthiomethyl]-3-cephem-4-carboxylic acid When 7-(2-aminomethylphenylacetamido)cephalosporanic acid sodium salt is reacted with 1-(2-ureidoethyl)tetrazole-5-thiol sodium salt by the procedure described in Example 1 and the product is converted to the free acid as described therein, the title compound is obtained.

EXAMPLE 7

7-Trifluoromethylthioacetamido-3-[1-(2-ureidoethyl)-tetrazol-5-ylthiomethyl]-3-cephem-4-carboxylic acid A solution of 1.88 g. (10.0 mmol.) of 1-(2-ureidoethyl)tetrazol-5-thiol, 0.840 g. of sodium bicarbonate and 5.45 g. (12.5 mmol.) of 7-trifluoromethylthioacetamidocephalosporanic acid sodium salt in 60 ml. of water is stirred at 70°–75° for 5 hours while maintaining the pH at 6.8 by addition of 5% aqueous sodium carbonate solution. The reaction mixture is cooled and diluted with water. Ethyl acetate is added and the mixture is acidified to pH 2.0 with 6N hydrochloric acid. The combined aqueous phases are further extracted with ethyl acetate and the extracts are dried (MgSO$_4$) and evaporated to dryness to give the title compound.

EXAMPLE 8

Reaction of the sodium salt of a cephalosporanic acid listed below:

7-(2,2,2-trifluoroethylthioacetamido)-cephalosporanic acid
7-trifluoromethylsulfinylacetamidocephalosporanic acid with 1-(2-ureidoethyl)tetrazole-5-thiol as described in the procedure of Example 7 gives the following compounds of this invention as final products:

7-(2,2,2-trifluoroethylthioacetamido)-3-[1-(2-ureidoethyl)tetrazol-5-ylthiomethyl]-3-cephem-4-carboxylic acid
7-trifluoromethylsulfinylacetamido-3-[1-(2-ureidoethyl)tetrazol-5-ylthiomethyl]-3-cephem-4-carboxylic acid.

EXAMPLE 9

7-Amino-3-[1-(2-ureidoethyl)tetrazol-5-ylthiomethyl]-3-cephem-4-carboxylic acid A solution of 11.29 g. (0.06 mol.) of 1-(2-ureidoethyl)-tetrazole-5-thiol in 120 ml. of acetone is added to a warm (45°) solution of 10.9 g. (0.04 mol.) of 7-aminocephalosporanic acid in a mixture of 220 ml. of water, 50 ml. of acetone and 8.4 g. (0.01 mol.) of sodium bicarbonate. The temperature is raised to 65° and the pH maintained at 7.4–7.6 by addition of aqueous sodium carbonate solution. After 3 hours, the acetone is removed in vacuo and the reaction mixture is cooled to 10° and adjusted to pH 3.5 by addition of dilute hydrochloric acid. The product is collected, washed with water and then acetone to give the title compound.

EXAMPLE 10

When an equivalent amount of an N-aminoalkylacetamide listed below:

N-(3-aminopropyl)acetamide
N-(4-aminobutyl)acetamide
N-(5-aminopentyl)acetamide is used in the procedure of Example 1 in place of N-(2-aminoethyl)acetamide and the resulting dithiocarbamates are treated with sodium azide to produce the corresponding 1-acetamidoalkyltetrazole-5-thiols which are converted to the 1-ureidoalkyl derivatives, all as described therein, the following 1-ureidoalkyltetrazole-5-thiols are obtained:

1-(3-ureidopropyl)tetrazole-5-thiol
1-(4-ureidobutyl)tetrazole-5-thiol
1-(5-ureidopentyl)tetrazole-5-thiol.

Reaction of the sodium salt of a 1-ureidoalkyltetrazole-5-thiol listed above with 7-D-mandelamidocephalosporanic acid sodium salt as described in the procedure of Example 1 followed by conversion of the salt formed to the free acid, gives the following compounds of this invention:

7-D-mandelamido-3-[1-(3-ureidopropyl)tetrazol-5-ylthiomethyl]-3-cephem-4-carboxylic acid
7-D-mandelamido-3-[1-(4-ureidobutyl)tetrazol-5-ylthiomethyl]-3-cephem-4-carboxylic acid
7-D-mandelamido-3-[1-(5-ureidopentyl)tetrazol-5-ylthiomethyl]-3-cephem-4-carboxylic acid.

Likewise, reaction of the substituted tetrazole thiols or the corresponding sodium salts listed above with any of the 7-acyl cephalosporanic acids mentioned herein or their corresponding salts according to procedures described herein gives the corresponding compounds of this invention.

EXAMPLE 11

7-(2,2,2-Trifluoroethylsulfinylacetamido)-3-[1-(2-ureidoethyl)tetrazol-5-ylthiomethyl]-3-cephem-4-carboxylic acid To a stirred solution of 5.7 g. (0.03 mol.) of 2,2,2-trifluoroethylsulfinylacetic acid and 3.45 g. (0.03 mol.) of N-hydroxysuccinimide in 50 ml. of tetrahydrofuran at 0° is added 6.2 g. (0.031 mol.) of dicyclohexylcarbodiimide. The reaction mixture is stirred at 0° for 1 hour then at 25° for 12 hours. The precipitate is filtered and washed with tetrahydrofuran and the filtrate is evaporated to dryness to give the activated ester of 2,2,2-trifluoroethylsulfinylacetic acid.

A suspension of 4.0 g. (0.01 mol.) of 7-amino-3-[1-(2-ureidoethyl)tetrazol-5-ylthiomethyl]-3-cephem-4-carboxylic acid in 50 ml. of dry dimethylformamide is treated with 2 ml. of triethylamine and the mixture is stirred for 15 minutes at 25°. A slight excess of 0.01 mol. of the activated ester of 2,2,2-trifluoroethylsulfinylacetic acid is added to the mixture and it is stirred an additional hour. The reaction mixture is evaporated to dryness and water and ethyl acetate are added to the residue. The layers are separated, the ethyl acetate layer is discarded, fresh ethyl acetate is added to the aqueous phase and it is acidified to pH 2.5 by addition of 6N hydrochloric acid. The mixture is filtered, the layers are separated and the aqueous phase is extracted with ethyl acetate. The combined extracts are washed with water, dried (MgSO₄) and evaporated to dryness to give the title compound.

In like manner, the 7-(2,2,2-trifluoroethylsulfinylacetamido) derivatives of other 7-amino-3-ureidoalkyltetrazole cephalosporins described above may be prepared.

EXAMPLE 12

7-Methylthioacetamido-3-[1-(2-ureidoethyl)tetrazol-5-ylthiomethyl]-3-cephem-4-carboxylic acid To a stirred, cooled (−20°) solution of 10.4 g. (0.026 mol.) of 7-amino-3-[1-(2-ureidoethyl)tetrazol-5-ylthiomethyl]-3-cephem-4-carboxylic acid in 220 ml. of 3% sodium bicarbonate and 220 ml. of acetone is added dropwise a solution of 3.66 g. (0.029 mol.) of methylthioacetyl chloride in 52 ml. of acetone, during which time the pH of the reaction mixture is maintained at 8.0 by addition of 10% sodium hydroxide. After addition the reaction mixture is stirred an additional 20 minutes at −15°, then is warmed to 25° and extracted with ether. The remaining aqueous phase is cooled, 250 ml. of ethyl acetate is added and the slurry is acidified with 3N hydrochloric acid. The layers are separated and the aqueous phase is extracted twice more with ethyl acetate. The combined extracts are dried (MgSO₄) and evaporated to dryness to yield the title compound.

EXAMPLE 13

7-(D-α-Formyloxyphenylacetamido)-3-[1-(2-ureidoethyl)tetrazol-5-ylthiomethyl]-3-cephem-4-carboxylic acid A mixture of 4.0 g. (0.01 mol.) of 7-amino-3-[1-(2-ureidoethyl)tetrazol-5-ylthiomethyl]-3-cephem-4-carboxylic acid, 3.97 g. (0.02 mol.) of the formate ester of D-mandeloyl chloride and 5 g. of sodium bicarbonate in 100 ml. of water and 140 ml. of acetone is stirred in the cold for 1 hour, then at 25° for 2 hours. The acetone is evaporated in vacuo and the remaining aqueous mixture is extracted with ethyl acetate. The aqueous solution is added with stirring to a cold mixture of 100 ml. of water and 200 ml. of ethyl acetate and the pH of the resulting mixture is adjusted to 2.0 by addition of 6N hydrochloric acid. The mixture is filtered, the layers are separated and the ethyl acetate layer is washed with water, dried (MgSO$_4$) and evaporated to dryness to give the title compound.

EXAMPLE 14

Acylation of 7-amino-3-[1-(2-ureidoethyl)tetrazol-5-ylthiomethyl]-3-cephem-4-carboxylic acid with an activated derivative of an acid listed below:

cyanoacetic
cyanomethylthioacetate acid
4-pyridylthioacetic acid
2-pyridone-N-acetic acid
4-pyridone-N-acetic acid as described in the procedure of Example 11 gives the following compounds of this invention:

7-cyanoacetamido-3-[1-(2-ureidoethyl)tetrazol-5-ylthiomethyl]-3-cephem-4-carboxylic acid
7-cyanomethylthioacetamido-3-[1-(2-ureidoethyl)tetrazol-5-ylthiomethyl]-3-cephem-4-carboxylic acid
7-(4-pyridylthioacetamido)-3-[1-(2-ureidoethyl)tetrazol-5-ylthiomethyl]-3-cephem-4-carboxylic acid
7-(2-pyridoneacetamido)-3-[1-(2-ureidoethyl)tetrazol-5-ylthiomethyl]-3-cephem-4-carboxylic acid
7-(4-pyridoneacetamido)-3-[1-(2-ureidoethyl)tetrazol-5-ylthiomethyl]-3-cephem-4-carboxylic acid.

EXAMPLE 15

Reaction of a cephalosporanic acid listed below or its corresponding salt:

7-(α-hydroxy-2-thienylacetamido)cephalosporanic acid
7-(α-carboxy-2-thienylacetamido)cephalosporanic acid
7-(α-sulfophenylacetamido)cephalosporanic acid with 1-(2-ureidoethyl)tetrazole-5-thiol sodium salt by procedures described hereinabove gives, after conversion of the product to the free acid, the following compounds of this invention:

7-(α-hydroxy-2-thienylacetamido)-3-[1-(2-ureidoethyl)tetrazol-5-ylthiomethyl]-3-cephem-4-carboxylic acid
7-(α-carboxy-2-thienylacetamido)-3-[1-(2-ureidoethyl)tetrazol-5-ylthiomethyl]-3-cephem-4-carboxylic acid
7-(α-sulfophenylacetamido)-3-[1-(2-ureidoethyl)tetrazol-5-ylthiomethyl]-3-cephem-4-carboxylic acid.

EXAMPLE 16

7-(2,2,2-Trifluoroethylsulfonylacetamido)-3-[1-(2-ureidoethyl)tetrazol-5-ylthiomethyl]-3-cephem-4-carboxylic acid To a solution of 8.6 g. (0.019 mol.) of 7-amino-3-[1-(2-ureidoethyl)tetrazol-5-ylthiomethyl]-3-cephem-4-carboxylic acid t-butyl ester and 3.9 g. (0.019 mol.) of 2,2,2-trifluoroethylsulfonylacetic acid in tetrahydrofuran is added dropwise a solution of 3.9 g. (0.019 mol.) of dicyclohexylcarbodiimide in 100 ml. of tetrahydrofuran. The reaction mixture is stirred at 25° for 12 hours, then filtered and concentrated to about 10 ml. The residue is filtered and evaporated to dryness to give 7-(2,2,2-trifluoroethylsulfonylacetamido)-3-[1-(2-ureidoethyl)tetrazol-5-ylthiomethyl]-3-cephem-4-carboxylic acid t-butyl ester.

The ester is dissolved in acetonitrile and trifluoroacetic acid is added. The solution is stirred for 3 hours, then evaporated to dryness to give the title compound.

Likewise, 7-(2,2,2-trifluoroethylsulfonylacetamido) derivatives of the other 7-amino-3-substituted tetrazole cephalosporins disclosed herein are prepared.

EXAMPLE 17

An injectable pharmaceutical composition is formed by adding sterile water or sterile saline solution (2 ml.) to 500 mg. of 7-D-mandelamido-3-[1-(2-ureidoethyl)tetrazol-5-ylthiomethyl]-3-cephem-4-carboxylic acid sodium salt.

Pharmaceutical compositions of the other antibacterial compounds disclosed above may be formulated in a similar manner.

EXAMPLE 18

A tablet or capsule is formed from 500 mg. of 7-D-mandelamido-3-[1-(2-ureidoethyl)tetrazol-5-ylthiomethyl]-3-cephem-4-carboxylic acid, 250 mg. of lactose and 75 mg. of magnesium stearate.

Tablets or capsules of the other antibacterial compounds disclosed above may be formulated in a similar manner.

What is claimed is:

1. A compound of the formula:

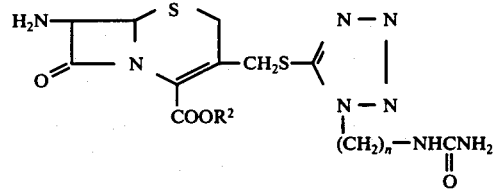

in which:
  $n$ is two to five; and
  $R^2$ is hydrogen or a protecting ester group.

2. A compound according to claim 1 in which $R^2$ is hydrogen, benzhydryl, t-butyl, trichloroethyl, benzyl, benzyloxymethyl, p-nitrophenyl, p-methoxyphenyl, p-methoxybenzyl or p-nitrobenzyl.

3. A compound according to claim 2 in which $n$ is two.

4. A compound according to claim 3, said compound being 7-amino-3-[1-(2-ureidoethyl)tetrazol-5-ylthiomethyl]-3-cephem-4-carboxylic acid.

* * * * *